(12) United States Patent
Park et al.

(10) Patent No.: US 8,481,592 B2
(45) Date of Patent: Jul. 9, 2013

(54) USES OF SESQUITERPENE DERIVATIVES

(75) Inventors: Tae-Sun Park, Seoul (KR); Ha-Won Kim, Seoul (KR)

(73) Assignee: Kwang Dong Pharm Co., Ltd., Seoul (KR)

( * ) Notice: Subject to any disclaimer, the term of this patent is extended or adjusted under 35 U.S.C. 154(b) by 126 days.

(21) Appl. No.: 13/058,264

(22) PCT Filed: Oct. 20, 2008

(86) PCT No.: PCT/KR2008/006198
§ 371 (c)(1),
(2), (4) Date: Mar. 7, 2011

(87) PCT Pub. No.: WO2010/030054
PCT Pub. Date: Mar. 18, 2010

(65) Prior Publication Data
US 2012/0129924 A1    May 24, 2012

(30) Foreign Application Priority Data

Sep. 11, 2008 (KR) .................. 10-2008-0089971

(51) Int. Cl.
*A61K 31/335* (2006.01)
(52) U.S. Cl.
USPC ...................................... 514/475
(58) Field of Classification Search
USPC ............. 514/475; 560/249; 568/817
See application file for complete search history.

(56) References Cited

U.S. PATENT DOCUMENTS

| | | |
|---|---|---|
| 6,942,967 B1 | 9/2005 | Harosh |
| 6,987,131 B1 | 1/2006 | Burzynski |
| 7,022,722 B2 | 4/2006 | Druzgala et al. |
| 7,071,195 B2 | 7/2006 | Dax et al. |
| 7,799,782 B2 * | 9/2010 | Munson et al. ............ 514/234.5 |
| 2005/0271755 A1 | 12/2005 | Raskin et al. |

FOREIGN PATENT DOCUMENTS

| | | |
|---|---|---|
| JP | 06-321884 A | 11/1994 |
| KR | 10-0711028 B1 | 4/2007 |

OTHER PUBLICATIONS

Tognolini et al. CAS: 144: 460278, 2006.*
Kawasaki's CAS: 138: 242863, 2003.*
Thies et al. CAS: 70: 80783, 1969.*
Duke et al., "Medicinal Plants of China," Library of Congress Catalog Record, 1985, bibliography, p. 1.
Luu et al., "Conifers of Vietnam," Darwin Initiative, 2004, pp. 1-94.
Duquesnoy et al., "Composition of a Pyrolytic Oil from *Cupressus funebris* Endl. of Vietnamese Origin," Flavour and Fragrance Journal, 2006, vol. 21, pp. 453-457.
R.P. Adams, "Essential Oils and Waxes," Modern Methods of Plant Analysis, 1991, vol. 12, pp. 159-173.
Laurence G. Cool, "Ent-Daucane and Acorane Sesquiterpenes from xCupressocyparis leylandii foliage," Phytochemistry, 2001, vol. 58, pp. 969-972.
Erdtman et al., "The Chemistry of the Natural Order Cupressales," 1957, Acta Chemica Scandinavica, vol. 11, pp. 1157-1161.
Emami et al., "Chemical and Antimicrobial Studies of *Cupressus sempervirens* L. and *C. horizentalis* Mill. Essential Oils," Iranian Journal of Pharmaceutical Sciences, 2006, vol. 2, No. 2, pp. 103-108.
Srikrishna et al., "Synthesis of (+/−)-ar-Macrocarpene," Synthetic Communications, 2007, vol. 37, pp. 2855-2860.
Ngo et al., "Synthesis of Sesquiterpene Allylic Alcohols and Sesquiterpene Dienes from *Cupressus bakeri* and *Chamaecyparis obtusa*," J. Chem. Soc., Perkin Trans., 2000, vol. 1, pp. 189-194.

* cited by examiner

*Primary Examiner* — Rei-tsang Shiao
(74) *Attorney, Agent, or Firm* — Sughrue Mion, PLLC

(57) ABSTRACT

The present invention relates to a pharmaceutical composition for preventing or treating hyperlipidemia, fatty liver, diabetes and obesity comprising a sesquiterpene derivative as an active ingredient. The sesquiterpene derivatives of the present invention leads to decrease in body fat weight, visceral fat weight and total cholesterol levels, triglyceride of plasma and liver tissue, blood glucose and blood insulin levels in a fast state, finally exhibiting efficacies on prevention or treatment of hyperlipidemia, fatty liver, diabetes and obesity.

3 Claims, 2 Drawing Sheets
(2 of 2 Drawing Sheet(s) Filed in Color)

Fig. 2

| | Conc(ug/ml) | 1 | 10 | 100 |
|---|---|---|---|---|
| Control | | +4 | | |
| Cedryl epoxide | | +4 | +3 | +2 |
| Cedryl formate | | +3 | +1 | +1 |
| Methyl cedryl ether | | +1 | +2 | +2 |
| (−)-clovene | | +2 | +2 | +2 |
| (+)-8(15)-cedren-9-ol | | +2 | +1 | +2 |
| (+)-Sativene | | +2 | +2 | +1 |
| (−)-Epicedrol | | +1 | +1 | +3 |
| Methyl cedryl ketone | | +3 | +2 | +1 |
| Cedrenal | | +2 | +1 | +1 | ate/palpitations, vertigo, and the like.

USES OF SESQUITERPENE DERIVATIVES

CROSS REFERENCE TO RELATED APPLICATIONS

This application is a National Stage of International Application No. PCT/KR2008/006198, filed on Oct. 20, 2008, which claims priority from Korean Patent Application No. 10-2008-0089971 filed on Sep. 11, 2008, the contents of all of which are incorporated herein by reference in their entirety.

BACKGROUND OF THE INVENTION

1. Field of the Invention

The present invention relates to a composition for preventing or treating hyperlipidemia, fatty liver, diabetes or obesity, comprising an extract of the genus *Cupressus* or a sesquiterpene derivative.

2. Description of the Related Art

Changes in life styles and living environments result in a pathogenic increase of visceral fat obesity in modern people. Frequent occurrence of visceral obesity in turn leads to a rapid increase in development of metabolic syndromes which are accompanied by diabetes, hypertension, lipid metabolism disorders, insulin resistance and the like. These attendant diseases increase a mutual risk factor and are common diseases which are associated with a variety of metabolic changes such as senescence, stress conditions, compromised immune function and the like.

According to the 2005 National Health and Nutrition Survey, 32% of Korean adults over 20-old age were found to suffer from obesity (35.2% of men and 28.3% of women). Recently, the incidence of childhood obesity is also soaring in Korea. According to the 2005 survey data, 11.3% of primary school children, 10.7% of junior high school students, and 16% of senior high school students were diagnosed with obesity (body mass index (BMI)≧25 kg/m$^2$). Further, overweight (BMI ≧23 kg/m$^2$) or 17% of obese juveniles showed metabolic syndrome.

Then, such an increase in the overweight and obese population contributes to a rise in the prevalence rate of chronic diseases. For example, according to the 2005 survey data, the prevalence rates of hypertension (30.2% of male and 25.6% of female), diabetes (9.0% of male and 7.2% of female), and hypercholesterolemia (7.5% of male and 8.8% of female) in Korean people over the age of 30 were significantly higher than that in other countries.

Based on the survey data, obesity may result in an estimated socioeconomic loss of approximately 1.017 trillion won in 2001. To this end, the Korean Health Plan 2010 was released by the Ministry of Health and Welfare as its public health policy. According to this white paper, main goals were established to accomplish an adult obesity rate of less than 20% and a juvenile obesity rate of less than 15%. As an implementation strategy to achieve these goals, an attempt was tried to find a precise definition and measurement method of obesity.

The best therapeutic effects on obesity can be achieved only with a combination of diet therapy, exercise therapy and behavior modification therapy. However, these therapeutic methods require plenty of time and effort in conjunction with difficulty in practice. For these reasons, anti-obesity drugs or diet products are widely used. However, orlistat, which is currently used as an anti-obesity drug, suffers from adverse side effects such as steatorrhea (fatty stools), enteric gas production, and flatus. Another anti-obesity drug, sibutramine, is also known to have adverse side effects such as headache, thirst, anorexia, insomnia, constipation and the like. Further, orlistat inhibits absorption of vitamin D and E, whereas administration of phentermine and sibutramine results in adverse side effects such as increased heart rate/palpitations, vertigo, and the like.

Recently, values and demands for herbal or natural medicines are increasing in view of adverse side effects of synthetic drugs and limitations of Western medicine in treating chronic diseases. To cope with this trend, the present inventors have screened an anti-obesity substance from a variety of wild or volunteer plants and then gave attention to *Cupressus funebris*.

*Cupressus funebris* is an evergreen tall tree that belongs to the genus *Cupressus*, which is widely distributed throughout warm temperate regions lower than 2,000 m from central and southwestern China to Vietnam. Its scientific name is also called *Chamaecypris funebris* and it's common name is Chinese weeping cypress.

It can grow in very acid sandy or clay soil. It requires well-drained and dry soil but it cannot grow well in the shade. It is a medium-sized coniferous tree growing to 20-35 m tall, with a trunk up to 2 m diameter. The leaves are scale-like up to 5 mm long on strong leaf shoots.

It has been used in the treatment of bleeding piles or excessive menstrual flow in China (J. A. Duke and E. S. Ayensu, *Medcinal Plants of China, pp.* 705, Reference Publications, Inc., 1985). It has been used in the manufacture of perfume, ingredient of essential oil, perfume of soap and shampoo in Vietnam (Luu and Thomas, 2004. p. 20-22, *Conifers of Vietnam*, Darwin Initiative). Essential oils by steam distillation of the wood of *Cupressus funebris* have been used in the ingredient of perfume, and there are a lot of monoterpenes in the leaf but the wood mainly contains sesquiterpenes. Sesquiterpenes are a class of terpenes that consist of three isoprene units and have the molecular formula $C_{15}H_{24}$. Although sesquiterpenes comprise 0, 1, 2 or 3 rings, the major sesquiterpenes in *Cupressus funebris* are tricyclic compounds. There are many kinds of sesquiterpenes in the wood of *Cupressus funebris* such as thujopsene (29.9%), alpha-cedrene (26.4%), beta-cedrene (9.2%), cedrol (9.6%), widdrol (9.5%), alpha-funebrene (0.7%), beta-funebrene (0.2%), cedryl acetate (0.1%) (Duquesnoy et al., 2006, *Flavour and Fragrance Journal*, 21: 453-457; Adams, 1991, *Modern Methods of Plant Analysis New Series, vol.* 12, pp. 159-173).

It was also reported that many kinds of plants belonging to the genus *Cupressus* such as *Cupressus macnabiana* (Laurence G. Cool, *Phytochemistry,* 58(6):969-972 (2001)), *Cupressus nootkatensis* (Erdtman, H. et al., *Acta Chem. Scand.,* 11:1157-1161 (1957)), *Cupressus sempervirens* (Seyyed Ahmad Emami et al., *Iranian Journal of Pharmaceutical Sciences,* 2(2):103-108 (2006)), *Cupressus macrocarpa* (Srikrishna et al., *Synthetic Communications,* 37(17): 2855-2860 (2007)), *Cupressus bakeri* (Koon-Sin Ngo et al., *J. Chem. Soc., Perkin Trans.* 1, 189-194 (2000)) include sesquiterpenes.

Various tricyclic sesquiterpene derivatives can be synthesized by an organic synthetic method, and most of the derivatives can be synthesized by semi-synthetic method. Representative synthetic or semi-synthetic sesquiterpene derivatives are cedrene epoxide ($C_{15}H_{24}O$), cedryl formate ($C_{16}H_{26}O_2$), methyl cedryl ether ($C_{16}H_{28}O$), cloven ($C_{15}H_{24}$), neoclovene ($C_{15}H_{24}$), 8(15)-cedren-9-ol ($C_{15}H_{24}O$), sativene ($C_{15}H_{24}$), epicedrol ($C_{15}H_{26}O$), methyl cedryl ketone ($C_{17}H_{26}O$) and cedrenol ($C_{15}H_{24}O$).

U.S. Pat. No. 7,071,195 discloses a method for treating obesity with amine or amide derivatives acting as ligands for neuropeptide Y Y5. U.S. Pat. No. 702,722 discloses a thiazolidinedione derivative for treating diabetes, hyperlipidemia or obesity.

U.S. Pat. No. 6,987,131 describes a composition for treating hyperlipidemia including phenylacetylglutamine, phenylacetylisoglutamine or phenylacetic acid. U.S. Pat. No. 6,942,967 suggests apobec-1 protein as a target molecule for treating arteriosclerosis, hyperlipidemia, obesity and diabetes.

Throughout this application, various publications and patents are referred and citations are provided in parentheses. The disclosures of these publications and patents in their entities are hereby incorporated by references into this application in order to fully describe this invention and the state of the art to which this invention pertains.

DETAILED DESCRIPTION OF THIS INVENTION

The present inventors have made intensive researches to develop a natural compound having anti-obesity, anti-hyperlipidemia and/or anti-diabetes efficacies. As a result, we have discovered an extract of *Cupressus funebris* or *Chamaecypris funebris* belonging to the genus *Cupressus*, a sesquiterpene derivative from *Cupressus funebris* or *Chamaecypris funebris*, and a synthetic sesquiterpene derivative with a structure similar to a derivative thereof have efficacies described above.

Accordingly, it is an object of this invention to provide a composition comprising a sesquiterpene derivative as an active ingredient for preventing or treating hyperlipidemia, fatty liver, diabetes or obesity.

It is another object of this invention to provide a method for preparing a sesquiterpene derivative from the genus *Cupressus*.

It is still another object of this invention to provide a method for preventing or treating hyperlipidemia, fatty liver, diabetes or obesity.

Other objects and advantages of the present invention will become apparent from the following detailed description together with the appended claims and drawings.

In one aspect of this invention, there is provided a composition for preventing or treating hyperlipidemia, fatty liver, diabetes or obesity, comprising a sesquiterpene derivative as an active ingredient.

The sesquiterpene derivatives are represented by the following formula I, II or III:

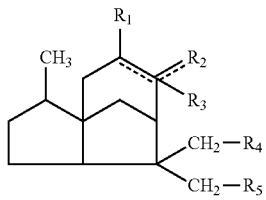
(I)

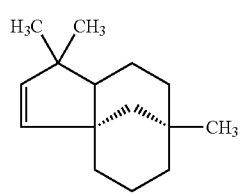
(II)

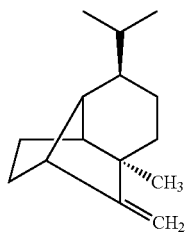
(III)

wherein $R_1$ represents hydrogen, hydroxy, halo, $C_1$-$C_3$ alkyl or —CO—$R_6$; $R_6$ represents hydrogen or $C_1$-$C_3$ alkyl; $R_2$ represents hydrogen, hydroxy or $C_1$-$C_3$ alkyl; $R_1$ and $R_2$ may be taken together to form an epoxide; $R_3$ represents hydrogen, hydroxy, $C_1$-$C_3$ alkyl, —O—CO—$R_7$ or $C_1$-$C_3$ alkoxy; $R_7$ represents hydrogen or $C_1$-$C_3$ alkyl; $R_4$ represents hydrogen, hydroxy or $C_1$-$C_3$ alkoxy; $R_5$ represents hydrogen, hydroxy or $C_1$-$C_3$ alkoxy; ═══ represents a single or a double bond; when ═══ in the ring is a double bond, $R_2$ represents hydrogen, hydroxy or $C_1$-$C_3$ alkyl; and when ═══ next to $R_2$ is a double bond, $R_2$ represents $CH_2$; when $R_2$ is methyl, $R_3$ is hydroxy and $R_5$ is hydrogen, $R_4$ is not hydrogen.

In another aspect of this invention, there is provided a method for preventing or treating hyperlipidemia, fatty liver, diabetes or obesity, which comprises administering to a subject a composition comprising a sesquiterpene derivative as an active ingredient.

The present inventors have made intensive researches to develop a natural compound having anti-obesity, anti-hyperlipidemia and/or anti-diabetes efficacies. As a result, we have discovered an extract of *Cupressus funebris* or *Chamaecypris funebris* belonging to the genus *Cupressus*, a sesquiterpene derivative from *Cupressus funebris* or *Chamaecypris funebris*, and a synthetic sesquiterpene derivative with a structure similar to a derivative thereof have efficacies described above.

According to a preferable embodiment, wherein $R_1$ represents hydrogen, hydroxy or —CO—$R_6$; $R_6$ represents $C_1$-$C_3$ alkyl; $R_2$ represents hydroxy or $C_1$-$C_3$ alkyl; $R_1$ and $R_2$ may be taken together to form an epoxide; $R_3$ represents hydroxy, $C_1$-$C_3$ alkyl, —O—CO—$R_1$ or $C_1$-$C_3$ alkoxy; $R_7$ represents hydrogen or $C_1$-$C_3$ alkyl; $R_4$ represents hydrogen or hydroxy; $R_5$ represents hydrogen or hydroxy; ═══ represents a single or a double bond; when ═══ in the ring is a double bond, $R_2$ represents $C_1$-$C_3$ alkyl; when ═══ next to $R_2$ is a double bond, $R_2$ represents $CH_2$; and when $R_2$ is methyl, $R_3$ is hydroxy and $R_5$ is hydrogen, $R_4$ is not hydrogen.

According to a preferable embodiment, wherein $R_1$ represents hydrogen, hydroxy or —CO—$CH_3$; $R_2$ represents hydroxy or —$CH_3$; $R_1$ and $R_2$ may be taken together to form an epoxide; $R_3$ represents hydroxy, —$CH_3$, —O—CO—$CH_3$ or —O—$CH_3$; $R_4$ represents hydrogen or hydroxy; $R_5$ represents hydrogen or hydroxy; ═══ represents a single or a double bond; when ═══ in the ring is a double bond, $R_2$ represents $CH_3$; when ═══ next to $R_2$ is a double bond, $R_2$ represents $CH_2$; and when $R_2$ is methyl, $R_3$ is hydroxy and $R_5$ is hydrogen, $R_4$ is not hydrogen.

In Formulae defined by the present compound, the term "$C_1$-$C_3$ alkyl" is defined herein to be straight chain or branched chain saturated hydrocarbon group from $C_1$ to $C_3$, i.e., lower alkyl including methyl, ethyl, n-propyl, isopropyl. The term used herein "halo" means halogen atoms, for instance including fluoro, chloro, bromo, and iodo, preferably fluoro, chloro or bromo. The term "alkoxy" means —O alkyl groups. Where substituted with $C_1$-$C_3$ substituted alkyl groups, halo preferably chloro or fluoro, more preferably fluoro substituted alkyl substituents may be used. The term "epoxide" means a cyclic ether compound that contains one oxygen atom as part of a three-membered ring with carbon atoms.

The compound represented by the formula I, II or III exhibits prevention or treatment efficacies on hyperlipidemia, fatty liver and obesity. As demonstrated in examples below, the sesquiterpene derivatives contribute to decrease in body fat weight, visceral fat weight, total cholesterol levels, and triglyceride level in plasma and liver, finally exhibiting prevention or treatment efficacies on hyperlipidemia, fatty liver and obesity. In addition, the sesquiterpene derivatives contribute to decrease significantly both blood glucose and blood insulin levels in a fast state, exhibiting improvement efficacies on type II diabetes or insulin resistance and metabolic inflammation closely associated thereof.

According to a preferable embodiment, the sesquiterpene derivatives are contained in extracts or fractions of the genus *Cupressus*.

The genus *Cupressus*, an evergreen tall tree, is one of several genera within the family Cupressaceae that have the common name cypress. About 20 species belong to *Cupressus*, which are grown as decorative trees or grown for their timber. They are native to scattered localities in mainly warm temperate regions in the northern hemisphere, including Asia, Europe and North America. They are large shrubs growing to 25 m tall, especially pyramid-shaped when young.

The *Cupressus* tree useful in the present invention may include any *Cupressus* containing sesquiterpene derivatives, but not limited to, preferably *Cupressus* macnabiana (Laurence G. Cool, *Phytochemistry*, 58(6): 969-972 (2001)), *Cupressus* nootkatensis (Erdtman, H. et al., *Acta Chem. Scand.*, 11: 1157-1161 (1957)), *Cupressus sempervirens* (Seyyed Ahmad Emami et al., *Iranian Journal of Pharmaceutical Sciences*, 2(2): 103-108 (2006)), *Cupressus macrocarpa* (Srikrishna et al., *Synthetic Communications*, 37(17): 2855-2860 (2007)), *Cupressus bakeri* (Koon-Sin Ngo et al., *J. Chem. Soc., Perkin Trans.* 1, 189-194 (2000)) or *Cupressus funebris*, and most preferably *Cupressus funebris*.

The extract of *Cupressus* sp. containing sesquiterpene derivatives as active ingredients may be obtained by extracting *Cupressus* sp. (preferably the xylem of *Cupressus* sp.) with various extraction solvents: preferably, (a) absolute or water-bearing lower alcohol containing 1-4 carbon atoms (methanol, ethanol, propanol, butanol, n-propanol, iso-propanol and n-butanonl etc.), (b) mixture of lower alcohol and water, (c) acetone, (d) ethyl acetate, (e) chloroform, (f) 1,3-butylene glycol, (g) hexane, (h) diethylether, (i) butylacetate, and (j) water.

The fraction of the genus *Cupressus* containing sesquiterpene derivatives refers to a isolated or purified form obtained by further isolation or purification of *Cupressus* sp. extracts. For instance, it could be appreciated that any fraction obtained using a variety of additional purification methods such as an ultrafiltration with defined molecular weight cut-off value and various chromatography (designed for purification dependent upon size, charge, hydrophobicity and affinity) is included in the present fractions. The sesquiterpene derivatives obtained from the fractions used in the present invention may include any sesquiterpene derivatives, but not limited to, preferably cedryl acetate represented by the following formula IV, α-cedrene represented by the following formula V, β-cedrene represented by the following formula VI), α-funebrene represented by the following formula VII or β-funebrene represented by the following formula VIII, and more preferably cedryl acetate, α-cedrene or β-cedrene.

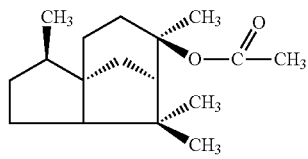

(IV)

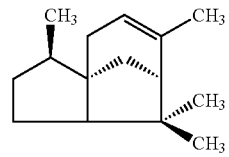

(V)

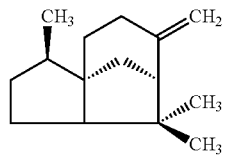

(VI)

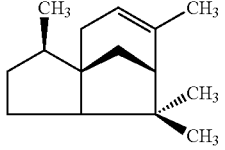

(VII)

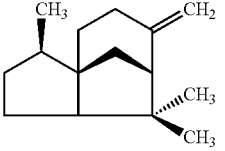

(VIII)

In addition, sesquiterpene derivatives may be chemically synthesized.

According to a preferable embodiment, the sesquiterpene derivatives comprise any sesquiterpene derivatives chemically synthesized in addition to sesquiterpene derivatives isolated from the genus *Cupressus*. More preferably, the sesquiterpene derivatives comprise cedrene epoxide represented by the following formula IX, cedryl formate represented by the following formula X, methyl cedryl ether represented by the following formula XI), 8(15)-cedren-9-ol represented by the following formula XII), epicedrol represented by the following formula XIII), methyl cedryl ketone represented by the following formula XIV) or cedrenol represented by the following formula XV. Most preferably, the sesquiterpene derivatives comprise cedrene epoxide, methyl cedryl ether, methyl cedryl ketone or cedrenol.

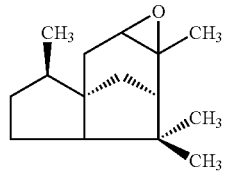

(IX)

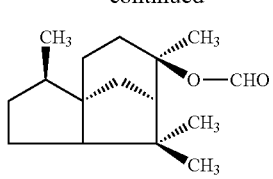
(X)

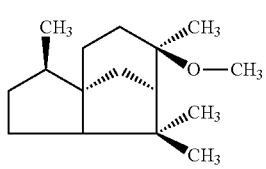
(XI)

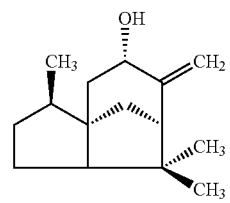
(XII)

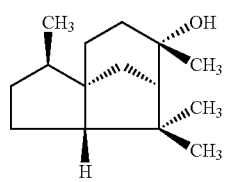
(XIII)

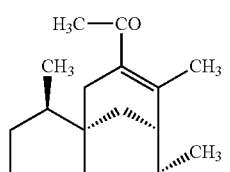
(XIV)

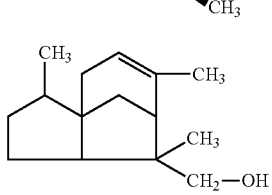
(XV)

In still another aspect of this invention, there is provided a pharmaceutical composition or a food composition for preventing or treating hyperlipidemia, fatty liver, diabetes or obesity, comprising a sesquiterpene derivative as an active ingredient.

The pharmaceutical composition may contain a pharmaceutically acceptable carrier. In the pharmaceutical compositions of this invention, the pharmaceutically acceptable carrier may be conventional one for formulation, including lactose, dextrose, sucrose, sorbitol, mannitol, starch, rubber arable, potassium phosphate, arginate, gelatin, potassium silicate, microcrystalline cellulose, polyvinylpyrrolidone, cellulose, water, syrups, methyl cellulose, methylhydroxy benzoate, propylhydroxy benzoate, talc, magnesium stearate, and mineral oils, but not limited to. The pharmaceutical composition according to the present invention may further include a lubricant, a humectant, a sweetener, a flavoring agent, an emulsifier, a suspending agent, and a preservative. Details of suitable pharmaceutically acceptable carriers and formulations can be found in *Remington's Pharmaceutical Sciences* (19th ed., 1995), which is incorporated herein by reference.

The pharmaceutical composition of this invention may be administered orally or parenterally, and preferably orally.

A suitable dose of the pharmaceutical composition of the present invention may vary depending on pharmaceutical formulation methods, administration methods, the patient's age, body weight, sex, severity of diseases, diet, administration time, administration route, an excretion rate and sensitivity for a used pharmaceutical composition. Physicians of ordinary skill in the art can determine an effective amount of the pharmaceutical composition for desired treatment. Preferably, the pharmaceutical composition of the present invention is administered with a daily dose of 0.001-100 mg/kg (body weight).

According to the conventional techniques known to those skilled in the art, the pharmaceutical composition may be formulated with pharmaceutically acceptable carrier and/or vehicle as described above, finally providing several forms including a unit dose form and a multi-dose form. Non-limiting examples of the formulations include, but not limited to, a solution, a suspension or an emulsion in oil or aqueous medium, an extract, an elixir, a powder, a granule, a tablet and a capsule, and may further comprise a dispersion agent or a stabilizer.

The food composition may contain additional ingredients used in conventional food compositions as well as the extract of *Cupressus* sp. The food composition may comprise conventional additives for preparing food compositions, e.g., proteins, carbohydrates, lipids, nutritive substances and flavors. Non-limiting examples of natural carbohydrates include, but not limited to, monosaccharide (e.g., glucose and fructose), disaccharide (e.g., maltose and sucrose), oligosaccharide, polysaccharide (e.g., dextrin and cyclodextrin) and sugar alcohol (e.g., xylitol, sorbitol and erythritol). Non-limiting examples of flavors include, but not limited to, natural flavors (e.g., thaumatin and extract of *Stevia*) and synthetic flavors (e.g., saccharin and aspartame).

For example, where the food composition of this invention is provided as a drink, it may further comprise citric acid, liquefied fructose, sucrose, glucose, acetic acid, malic acid, fruit juices, *Eucommia ulmoides* extracts, jujube extracts and/or licorice extracts as well as the extract of *Cupressus* sp. as an active ingredient.

The present compositions comprising the extract of the genus *Cupressus* as an active ingredient lead to decreases in body fat weight, visceral fat weight and total cholesterol levels, triglyceride levels in plasma and liver, and blood glucose and blood insulin levels in a fast state, finally exhibiting prevention or treatment efficacies on hyperlipidemia, fatty liver and obesity.

The term used herein "hyperlipidemia" refers to diseases induced by elevated blood fat levels associated with abnormalities in fat metabolisms for triglycerides and cholesterol. More specifically, hyperlipidemia refers to conditions with elevated lipid levels such as triglycerides, LDL cholesterol, phospholipids and fatty acids and is often called as hypercholesterolemia.

The term used herein "fatty liver" means conditions with excessive accumulation of fats in liver resulting from lesions of fat metabolisms. This condition is a pathological cause for various diseases such as angina pectoris, myocardial infarction, stroke, arteriosclerosis and pancreatitis.

The term "diabetes" used herein refers to chronic diseases caused by relative or absolute insulin insufficiency leading to glucose-intolerance. The term "diabetes" is used to intend to encompass all types of diabetes, e.g., type I diabetes, type II diabetes and hereditary diabetes. type I diabetes is insulin-dependent diabetes caused mainly by β-cell disruption. type II diabetes is insulin-independent diabetes caused by insufficient insulin secretion after diet or insulin resistance.

According to a preferable embodiment, the present composition is used in prevention or treatment of type II diabetes, and more preferably type II diabetes associated with insulin resistance.

In still further aspect of this invention, there is provided a method for preparing the sesquiterpene derivatives, which comprises the steps of: (a) contacting an extraction solvent to the genus *Cupressus* to obtain an extract with anti-obesity effects; and (b) fractionating the extract and selecting a fraction with anti-obesity effects to isolate the sesquiterpene derivative.

The present method will be described in more detail as follows:

(a) Preparation of Extracts from the Genus *Cupressus*

The *Cupressus* sp. tree useful in the present invention may include any *Cupressus* sp. tree, preferably, *Cupressus macnabiana, Cupressus nootkatensis, Cupressus sempervirens, Cupressus macrocarpa, Cupressus* baked or *Cupressus funebris*, more preferably *Cupressus funebris*, and most preferably the xylem of *Cupressus funebris*.

The extraction solvent may include any solvent known to one of skill in the art. Preferably, the extraction solvent is a nonpolar solvent, more preferably one selected from the group consisting of dichloromethane, hexane, chloroform and ethylether, and most preferably dichloromethane.

According to a preferable embodiment, the filtration and concentration of extracts is carried out after extraction.

Anti-obesity effects of the extract are confirmed through anti-obesity tests using *Caenorhabditis elegans* (*C. elegans*).

(b) Isolation of Sesquiterpene Derivatives by Fractionation of Extracts

The fractionation of *Cupressus* sp. tree extracts may be performed in accordance with conventional fractionation or purification procedures. Most preferably, the fractionation is performed by applying the *Cupressus* sp. tree extract to a silica gel column.

According to a preferred embodiment, the step (b) is performed by applying the extract of the step (a) to a first silica gel column and performing elution under conditions to elute preferentially components with low polarity to obtain a fraction having anti-obesity activity. The elution may include any solvent known to one of skill in the art. Preferably, the extraction solvent is the nonpolar solvent, more preferably, one selected from the group consisting of dichloromethane, hexane, chloroform and ethylether, and most preferably dichloromethane and/or normal-hexane. For instance, the fractionation may be performed by dichloromethane gradient (starting with normal hexane and then with dichloromethane gradient).

The features and advantages of the present invention will be summarized as follows:

(a) The present invention provides a composition for preventing or treating hyperlipidemia, fatty liver, diabetes or obesity, comprising a sesquiterpene derivative represented by the formulae I, II or III as an active ingredient.

(b) The present composition can be prepared from the genus *Cupressus* or chemically synthesized.

(c) The present compositions comprising the extract of the genus *Cupressus* or a sesquiterpene derivative as an active ingredient lead to decrease in body fat weight, visceral fat weight and total cholesterol levels, triglyceride levels in plasma and liver, and blood glucose and blood insulin levels in a fast state, finally exhibiting prevention or treatment efficacies on hyperlipidemia, fatty liver, diabetes or obesity.

BRIEF DESCRIPTION OF THE DRAWINGS

The patent or application file contains at least one drawing executed in color. Copies of this patent or patent application publication with color drawings will be provided by the Office upon request and payment of the necessary fee.

FIG. 2 represents effects of sesquiterpene derivatives chemically synthesized on body fat levels of *C. elegans*. Numerals in photograph are fat content stained by Nile red. A low fat content was indicated by +1, whereas a high fat content was assigned with +4.

Figure 1:
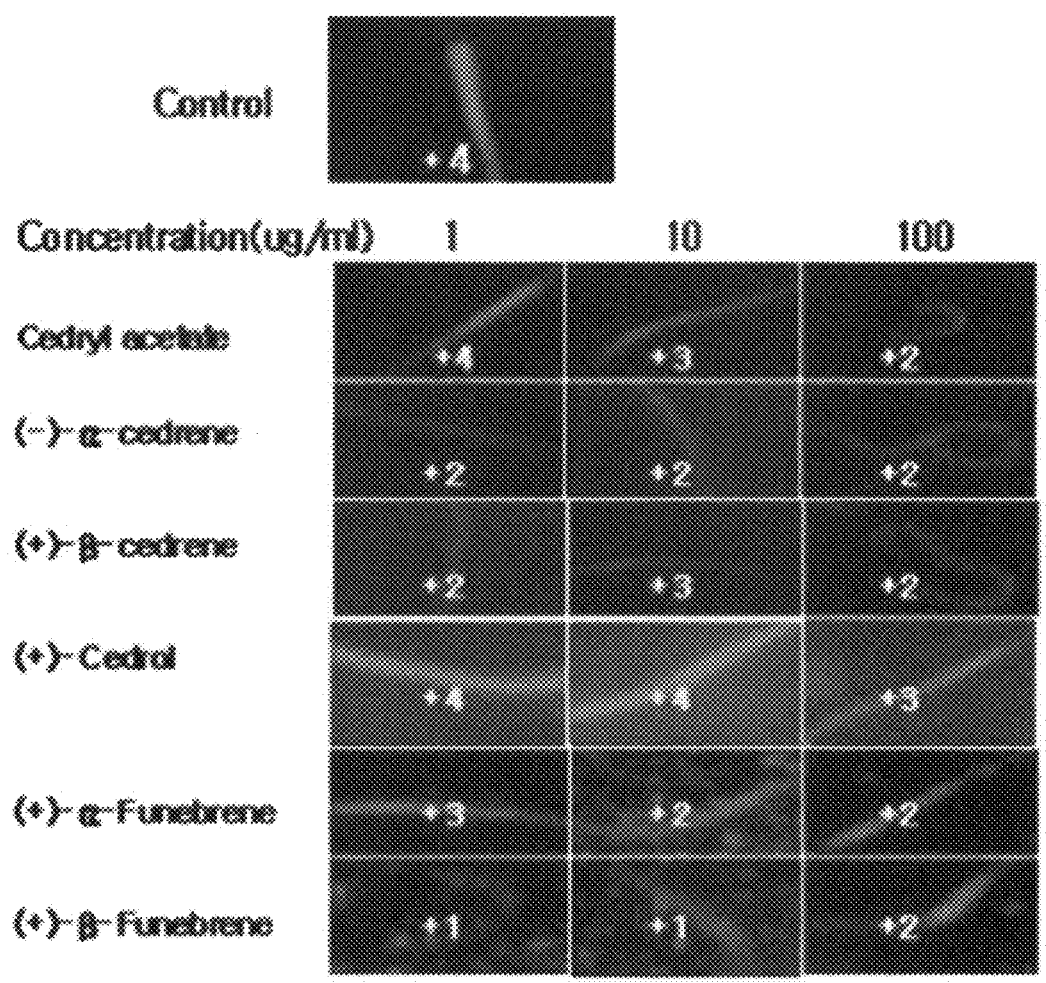
FIG. 1 represents effects of sesquiterpene derivatives isolated from the genus *Cupressus* on body fat levels of *C. elegans*. Numerals in photograph represent fat content stained by Nile red. A low fat content was indicated by +1, whereas a high fat content was assigned with +4.

The present invention will now be described in further detail by examples. It would be obvious to those skilled in the art that these examples are intended to be more concretely illustrative and the scope of the present invention as set forth in the appended claims is not limited to or by the examples.

EXAMPLES

Example 1

Fractionation of *Cupressus* sp. Extract and Isolation of Sesquiterpene Derivatives The xylem of *Cupressus funebris* belonging to *Cupressus* sp. was entirely dried in the shade, and then ground into powder by a grinder. Forty five L of dichloromethane ($CH_2Cl_2$) was added to 10 kg of the powder for extraction at 25° C. for 14 days. The extraction process was repeated twice. The primary extract and the secondary extract were combined and filtered, and the resulting filtrate was concentrated in a 50° C.-water bath under vacuum to afford 140 g of a total extract. After evaluation on anti-obesity effect of the total extract in *Caenorhabditis elegans*, the extract was further fractioned using a mass preparative silica gel column. The 140 g of the total extract were fractioned using the column having a diameter of 6.5 cm and a height of 80 cm and packed with silica gel (230-400 mesh, Merck, Germany). A total of six compounds (Compound-1, Compound-2, Compound-3, Compound-4, Compound-5 and Compound-6) were isolated using a developing solvent (starting with normal hexane and then with dichloromethane gradient from 0.1% to 1%). The anti-obesity effects of the compounds were evaluated.

Example 2

Structural Analysis of the Compounds Isolated from *Cupressus Funebris*

The mass analysis, $^1$H-NMR and $^{13}$C-NMR of the 6 compounds showed that Compound-1 is cedryl acetate, Compound-2 is (−)-α-cedrene, Compound-3 is (+)-β-cedrene, Compound-4 is (+)-cedrol, Compound-5 is (+)-α-funebrene and Compound-6 is (+)-β-funebrene. The instrumental analyses and chemical structures of the compounds were shown below.

Structural Analysis of Compound-1

Physical characteristics of the compound-1 were crystal powder, a melting point of 44-46° C., a chemical formula of $C_{17}H_{28}O_2$ and a molecular weight of 264 by the mass analysis.

The $^1$H-NMR analysis of compound-1 was carried out: $^1$H-NMR (400 MHz in $CDCl_3$) δ 0.83(d, J=7.2, 3H), 0.97 (s, 3H), 1.17 (s, 3H), 1.25-1.29 (1H), 1.30-1.45 (4H), 1.52 (s, 3H), 1.61-1.68 (1H), 1.78-1.82 (1H), 1.85-1.91 (1H), 1.95 (s, 3H), 2.00-2.03 (1H), 2.38-2.42 (1H).

In addition, the $^{13}$C-NMR spectra for compound-1 were obtained: $^{13}$C-NMR (150 MHz, in $CDCl_3$): δ(ppm) 25.8 (C1), 37.0 (C2), 41.0 (C3), 54.0 (C3a), 31.2 (C4), 33.2 (C5), 86.2 (C6), 56.9 (C7), 43.4 (C8), 56.7 (C8a), 41.3 (C9), 15.5 (C10), 25.3 (C11), 170.3 (C12), 22.8 (C13), 26.9 (C14), 28.4 (C15).

Compound-1 was identified to have the chemical formula of $C_{17}H_{28}O_2$ (cedryl acetate) by the above instrumental analysis. The chemical structure of compound-1 is represented by the formula below.

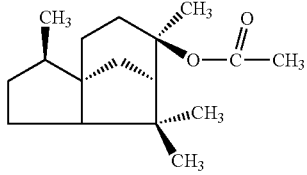

Structural Analysis of Compound-2

Physical characteristics of the compound-2 were liquid state, a chemical formula of $C_{15}H_{24}$ and a molecular weight of 204 by the mass analysis.

The $^1$H-NMR analysis of compound-2 was carried out: $^1$H-NMR (400 MHz in $CDCl_3$) δ 0.84(d, J=7.2, 3H), 0.95 (s, 3H), 1.02 (s, 3H), 1.33-1.42 (3H), 1.55-1.62 (1H), 1.63-1.64 (1H), 1.66-1.67 (3H), 1.69-1.71 (1H), 1.73-1.76 (1H), 1.78-1.87 (2H), 2.14-2.19 (1H), 5.22 (1H).

In addition, the $^{13}$C-NMR spectra for compound-2 were obtained: $^{13}$C-NMR (100 MHz in $CDCl_3$): δ(ppm) 24.8 (C1), 36.1 (C2), 41.5 (C3), 53.9 (C3a), 38.1 (C4), 119.2 (C5), 140.3 (C6), 54.9 (C7), 48.1 (C8), 59.0 (C8a), 40.7 (C9), 15.4 (C10), 24.7 (C11), 25.6 (C12), 27.7 (C13).

Compound-2 was identified to have the chemical formula of $C_{15}H_{24}$ ((−)-α-Cedrene) by the above instrumental analysis. The chemical structure of compound-2 is represented by the formula below.

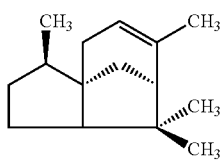

Structural Analysis of Compound-3

Physical characteristics of the compound-3 were liquid state, a chemical formula of $C_{15}H_{24}$ and a molecular weight of 204 by the mass analysis.

The $^1$H-NMR analysis of compound-3 was carried out: $^1$H-NMR (400 MHz in $CDCl_3$) δ 0.84(d, J=7.2, 3H), 0.94 (s, 3H), 0.97 (s, 3H), 1.18-1.21 (1H), 1.28-1.34 (1H), 1.36-1.45 (1H), 1.47-1.49 (1H), 1.51-1.58 (2H), 1.66-1.72 (1H), 1.75-1.83 (2H), 1.85-1.90 (1H), 2.19 (1H), 2.31-2.34 (2H), 4.58 (1H), 4.59 (1H).

In addition, the $^{13}$C-NMR spectra for compound-3 were obtained: $^{13}$C-NMR (150 MHz, in $CDCl_3$): δ(ppm) 25.7 (C1), 37.0 (C2), 42.1 (C3), 54.4 (C3a), 33.7 (C4), 29.7 (C5), 151.9 (C6), 60.7 (C7), 42.3 (C8), 56.4 (C8a), 45.1 (C9), 15.4 (C10), 107.6(C11), 25.9 (C12), 26.6 (C13).

Compound-3 was identified to have the chemical formula of $C_{15}H_{24}$ ((+)-β-Cedrene) by the above instrumental analysis. The chemical structure of compound-3 is represented by the formula below.

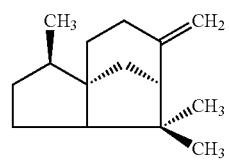

Structural Analysis of Compound-4

Physical characteristics of the compound-4 were crystal powder, a melting point of 55-59° C., a chemical formula of $C_{15}H_{26}O$ and a molecular weight of 222 by the mass analysis.

The $^1$H-NMR analysis of compound-4 was carried out: $^1$H-NMR ($CDCl_3$) δ 0.85(3H), 1.00 (3H), 1.26 (3H), 1.27-1.29 (1H), 1.32 (3H), 1.35-1.43 (4H), 1.51-1.58 (3H), 1.61-1.71 (3H), 1.78-1.89 (3H).

In addition, the $^{13}$C-NMR spectra for compound-4 were obtained: $^{13}$C-NMR (150 MHz, in $CDCl_3$): δ(ppm) 25.4 (C1), 37.0 (C2), 41.5 (C3), 54.1 (C3a), 31.6 (C4), 35.4 (C5), 75.1 (C6), 61.1 (C7), 43.4 (C8), 56.5 (C8a), 42.0 (C9), 15.6 (C10), 30.2 (C11), 27.7 (C12), 28.9 (C13).

Compound-4 was identified to have the chemical formula of $C_{15}H_{26}O$ ((+)-Cedrol) by the above instrumental analysis. The chemical structure of compound-4 is represented by the formula below.

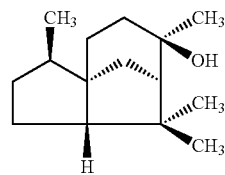

Structural Analysis of Compound-5

Physical characteristics of the compound-5 were liquid state, a chemical formula of $C_{15}H_{24}$ and a molecular weight of 204 by the mass analysis.

The $^1$H-NMR analysis of compound-5 was carried out: $^1$H-NMR ($CDCl_3$) δ 0.81-0.95(6H), 1.06 (s, 3H), 1.25-1.31 (1H), 1.32-1.46 (3H), 1.54-1.61 (2H), 1.61-1.64 (3H), 1.74-1.82 (1H), 1.92-1.99 (1H), 2.07-2.10 (1H), 2.15-2.32 (2H), 5.11 (1H).

In addition, the $^{13}$C-NMR spectra for compound-5 were obtained: $^{13}$C-NMR (150 MHz, in $CDCl_3$): δ(ppm) 21.8 (C1), 34.1 (C2), 37.2 (C3), 55.5 (C3a), 36.4 (C4), 119.0 (C5), 141.8 (C6), 58.1 (C7), 37.3 (C8), 61.2 (C8a), 36.6 (C9), 18.1 (C10), 18.4 (C11), 24.3 (C12), 243(C13).

Compound-5 was identified to have the chemical formula of $C_{15}H_{24}$ ((+)-α-Funebrene) by the above instrumental analysis. The chemical structure of compound-5 is represented by the formula below.

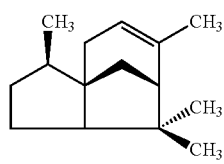

Structural Analysis of Compound-6

Physical characteristics of the compound-6 were liquid state, a chemical formula of $C_{15}H_{24}$ and a molecular weight of 204 by the mass analysis.

The $^1$H-NMR analysis of compound-6 was carried out: $^1$H-NMR (CDCl$_3$) δ 0.82-0.90(6H), 1.06 (s, 3H), 1.18-1.24 (1H), 1.24-1.35 (2H), 1.35-1.41 (1H), 1.41-1.50 (1H), 1.12 (1H), 1.62-1.68 (1H), 1.71-1.80 (1H), 1.91-1.95 (1H), 2.22-2.38 (2H), 2.55-2.58 (1H), 4.57 (1H), 4.58 (1H).

In addition, the $^{13}$C-NMR spectra for compound-6 were obtained: $^{13}$C-NMR (150 MHz, in CDCl$_3$): δ(ppm) 19.4 (C1), 34.1 (C2), 35.1 (C3), 55.6 (C3a), 32.5 (C4), 27.6 (C5), 152.5 (C6), 62.9 (C7), 37.3 (C8), 59.7 (C8a), 36.6 (C9), 18.3 (C10), 106.6 (C11), 21.6 (C12), 21.6 (C13).

Compound-6 was identified to have the chemical formula of $C_{15}H_{24}$ ((+)-β-Funebrene) by the above instrumental analyses. The chemical structure of compound-6 is represented by the formula below.

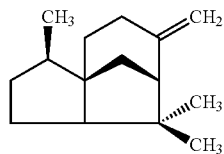

Example 3

Structures of Synthetic Chemical Compounds Similar to Sesquiterpene Compounds Isolated from *Cupressus Funebris*

The anti-obesity effects of the synthetic sesquiterpenes similar to 6 compounds isolated from *Cupressus Funebris* were evaluated. The chemical structures of the synthetic sequiterpene compounds evaluated are below. The synthetic sequiterpene compounds were purchased from companies, listed below.

Structural Analysis of Compound-7

Cedrene epoxide ($C_{15}H_{24}$), Zhejiang HuangYan Spice Co., Ltd. (China)

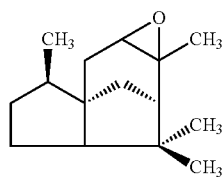

Structural Analysis of Compound-8

Cedryl formate ($C_{16}H_{26}O_2$), Sigma (USA)

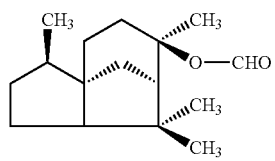

Structural Analysis of Compound-9

Methyl cedryl ether ($C_{16}H_{28}O$), Zhejiang HuangYan Spice Co., Ltd. (China)

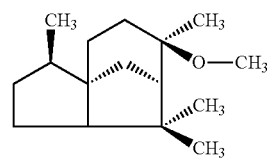

Structural Analysis of Compound-10

(−)-Clovene ($C_{15}H_{24}$), Sigma (USA)

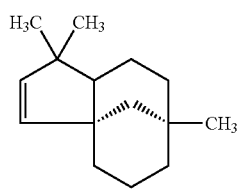

Structural Analysis of Compound-11

(+)-8(15)-Cedren-9-ol ($C_{15}H_{24}O$), Sigma (USA)

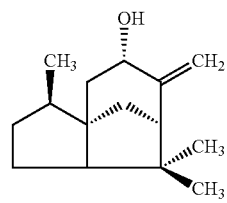

Structural Analysis of Compound-12

(+)-sativene ($C_{15}H_{24}$), Sigma (USA)

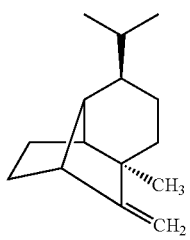

Structural Analysis of Compound-13

(−)—epicedrol ($C_{15}H_{26}O$), Sigma (USA)

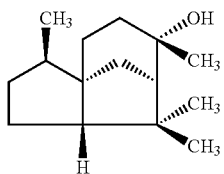

Structural Analysis of Compound-14

Methyl cedryl ketone, Zhejiang HuangYan Spice Co., Ltd. (China)

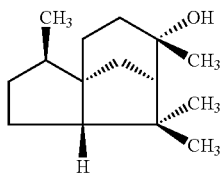

Structural analysis of Compound-15

Cedrenol ($C_{15}H_{24}O$), Jiangxi Zhangshu Crown Capital Fragrance Limited (China)

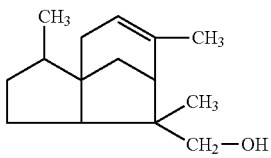

Example 4

Evaluation on Anti-Obesity Effects of 15 Sesquiterpene Compounds in C. elegans

Using a dissecting microscope (×50 magnification), C. elegans at the 4th stage (L4, the imaginal stage) was transferred to 3 ml of a cholesterol-supplemented S-medium (containing NaCl, $K_2HPO_4$, $KH_2PO_4$, cholesterol, citrate, trace metals, $CaCl_2$ and $MgSO_4$), and 100 μl of E. coli OP50 ($OD_{600}$=0.2) liquid-cultured overnight before 1 day of experiment was added thereto. The Pterocarpus indicus fraction sample was added to the liquid media containing C. elegans, followed by rotary culture in a dark room at 16° C. and 100 rpm. The water-insoluble sample was dissolved in DMSO and added to the culture media. The final concentration of DMSO was adjusted below 1%. 1% DMSO exhibited no effects on adipogenesis and growth of C. elegans. 24 hours after the sample was added to C. elegans, 30 μl of a Nile red dye at a concentration of 10 μg/ml was added (final concentration of Nile red was adjusted to 100 ng/ml) to the media, followed by continuous rotary culture for 2 days.

In order to arrest the locomotory movement of C. elegan, 20 μl of 0.3% $NaN_3$ was dropped on a slide glass to which 100 μl of C. elegans cultured in the presence of Nile red for 2 days was added. Under a fluorescence microscope, adipocytes of C. elegans emitting red fluorescence in a dark room were micrographed and compared with the control group to thereby determine the amount of fat. A low fat content was indicated by +1, whereas a high fat content was assigned with +4. Adult (L4 stage) C. elegans immediately prior to egg-laying were used in this Example. Therefore, the eggs were hatched after sample treatment and most of adult C. elegans were killed at 3 day post-treatment. A fat content was examined in C. elegans which had newly hatched and grown.

Anti-obesity effect of the total extract of Cupressus funebris was examined in C. elegans. The total extract at various concentrations (0, 1, 10 and 100 μg/ml) were added to the liquid media containing C. elegans. As represented in experimental results, Table 1, the total extract exhibited significant anti-obesity effects at a concentration of 10 μ/ml or higher.

TABLE 1

Anti-obesity effect of the total extract of Cupressus funebris to C. elegans.

| | Fat content Sample concentration (μg/ml) | | | |
|---|---|---|---|---|
| Items | 0 | 1 | 10 | 100 |
| Anti-obesity effect of the total extract | +4 | +4 | +3 | +2 |

(A low fat content was indicated by +1, whereas a high fat content was assigned with +4 in Table)

Each six compounds [(−)-α-cedrene, (+)-β-cedrene, (+)-cedrol, (+)-α-funebrene and (+)-β-funebrene] extracted from the xylem of Cupressus funebris, and nine compounds [cedrene epoxide, cedryl formate, methyl cedryl ether, (−)-clovene, (+)-8(15)-cedrene-9-ol, (+)-sativene, (−)-epicedrol, methyl cedryl ketone or cedrenol] having the similar structure was contacted to C. elegans in various concentrations (0, 1, 10, 100 μg/ml), and their inhibitory effect on adipogenesis was observed in the dark under a fluorescence microscope. As shown in both Table 2 and FIG. 1, total six sesquiterpene derivatives extracted from the plants had significantly inhibitory effect on adipogenesis in concentrations of 1, 10 or 100 μg/ml. Among them, (−)-α-cedrene, (+)-β-cedrene, (+)-α-funebrene and (+)-β-funebrene had notably inhibitory effect on adipogenesis even in a low concentration of 1 μg/ml.

TABLE 2

Anti-obesity effect of a component from Cupressus funebris in C. elegans.

| | Fat content Sample concentration (μg/ml) | | | |
|---|---|---|---|---|
| Item | 0 | 1 | 10 | 100 |
| Cedryl acetate | +4 | +4 | +3 | +2 |
| (−)-α-cedrene | +4 | +2 | +2 | +2 |
| (+)-β-cedrene | +4 | +2 | +3 | +2 |
| (+)-cedrol | +4 | +4 | +4 | +3 |
| (+)-α-funebrene | +4 | +3 | +2 | +2 |
| (+)-β-funebrene | +4 | +1 | +1 | +2 |

(A low fat content was indicated by +1, whereas a high fat content was assigned with +4 in Table)

In addition, anti-obesity effect of synthetic sesquiterpene compounds to C. elegans is examined. As shown in both Table 3 and FIG. 2, all compounds had significantly inhibitory effect on adipogenesis in a concentration of 1, 10 or 100 μg/ml. Of them, cedryl formate, methyl cedryl ether, (−)-clovene, (+)-8(15)-cedrene-9-ol, (+)-sativene, (−)-epicedrol, methyl cedryl ketone and cedrenol had notably inhibitory effect on adipogenesis even in a low concentration of 1 μg/ml.

Therefore, it could be demonstrated that total 15 sesquiterpene derivatives may contribute to decrease in body fat weight and be used as an anti-obesity agent.

TABLE 3

Anti-obesity effect of synthetic derivatives in *C. elegans*.

| | Fat content Sample concentration (μg/ml) | | | |
|---|---|---|---|---|
| Item | 0 | 1 | 10 | 100 |
| cedrene epoxide | +4 | +4 | +3 | +2 |
| cedryl formate | +4 | +3 | +1 | +1 |
| methyl cedryl ether | +4 | +1 | +2 | +2 |
| (−)-clovene | +4 | +2 | +2 | +2 |
| (+)-8(15)-cedrene-9-ol | +4 | +2 | +1 | +2 |
| (+)-sativene | +4 | +2 | +2 | +1 |
| (−)-epicedrol | +4 | +1 | +1 | +3 |
| methyl cedryl ketone | +4 | +3 | +2 | +1 |
| cedrenol | +4 | +2 | +1 | +1 |

(A low fat content was indicated by +1, whereas a high fat content was assigned with +4 in Table)

All 15 sesquiterpene derivatives used in the present invention regardless of any form extracted in nature or obtained through synthesis are fat-soluble because they were easily dissolved in organic solvent having lower polarity than ethanol, but not water. Thus, it has an advantage with respect to feasible intake in the small intestine to take these compounds in an oral manner. In addition, each powder component and liquid component may be prepared as a final product of tablet and soft capsule, enabling to be taken in a feasible manner. The compounds having a boiling point below 100° C. is cedrene epoxide (boiling point: 94-95° C.), and the compounds having a boiling point below 200° C. is (+)-8(15)-cedrene-9-ol (boiling point: 166-168° C.) and cedrenol (boiling point: 166-169° C.). In addition, all other compounds have a boiling point above 200° C., and thus are very stable in room temperature. The physical characteristics of each compound are described as Table 4.

TABLE 4

The physical characteristics of the compounds.

| compound | Origin | Property | Solubility | Boiling point (° C.) |
|---|---|---|---|---|
| Cedryl acetate | Natural compound | Crystallized powder | Fat soluble | 200-203 |
| (−)-α-cedrene | Natural compound | Viscous liquid | Fat soluble | 261-262 |
| (+)-β-cedrene | Natural compound | Viscous liquid | Fat soluble | 263-264 |
| (+)-cedrol | Natural compound | Viscous liquid | Fat soluble | 252-253 |
| (+)-α-funebrene | Natural compound | Viscous liquid | Fat soluble | 253-254 |
| (+)-β-funebrene | Natural compound | Crystallized powder | Fat soluble | 273-274 |
| cedrene epoxide | Synthetic compound | Viscous liquid | Fat soluble | 94-95 |
| cedryl formate | Synthetic compound | Viscous liquid | Fat soluble | 308-309 |
| methyl cedryl ether | Synthetic compound | Viscous liquid | Fat soluble | 268-269 |
| (−)-clovene | Synthetic compound | Viscous liquid | Fat soluble | 261-263 |
| (+)-8(15)-cedrene-9-ol | Synthetic compound | Crystallized powder | Fat soluble | 166-168 |
| (+)-sativene | Synthetic compound | Viscous liquid | Fat soluble | 255-257 |
| (−)-epicedrol | Synthetic compound | Crystallized powder | Fat soluble | 277-278 |
| methyl cedryl ketone | Synthetic compound | Viscous liquid | Fat soluble | 272-273 |
| cedrenol | Synthetic compound | Crystallized powder | Fat soluble | 166-169 |

Example 5

Reduced Effects of 8 Sesquiterpene Compounds on Body Weight and Visceral Fat

Diet Preparation and Experimental Animal Breeding

Obesity-inducible diet used in the present experiment was high fat diet (HFD: 40% fat calorie, 17 g Lard+3% maize oil/100 g diet) developed by the present inventors and the composition of diet containing sesquiterpene compounds was equal to that of HFD but each 8 sesquiterpene compounds with a concentration of 0.2% was included in diet [cedryl acetate-containing diet, (−)-α-cedrene-containing diet, (+)-β-cedrene-containing diet, cedrene epoxide-containing diet, methyl cedryl ether-containing diet, methyl cedryl ketone-containing diet, cedrenol-containing diet and (+)-cedrol-containing diet]. The composition of diet is described in the following Table 5.

TABLE 5

The composition of diet.

| Component | Control (HFD) (g/kg diet) | Test group (g/kg diet) |
|---|---|---|
| Casein | 200 | 200 |
| DL-methionine | 3 | 3 |
| Maize starch | 111 | 109 |
| Sucrose | 370 | 370 |
| Cellulose | 50 | 50 |
| Maize oil | 30 | 30 |
| Lard | 170 | 170 |
| Vitamin mixture | 12 | 12 |
| Mineral mixture | 42 | 42 |
| Choline bitartrate | 2 | 2 |
| Cholesterole | 10 | 10 |
| tert-butylhydroquinone | 0.04 | 0.04 |
| Sesquiterpene compound | — | 2 |
| Total (g) | 1,000 | 1,000 |
| Fat (% calorie) | 39.0 | 39.0 |
| Total heat, kJ/kg diet | 19,315 | 19,315 |

6-old-week C57BL/63 male mice were adapted to laboratory environment during one week and divided into HFD control and 8 test groups according to randommized block design. And then, they were bred for 6 weeks. Diet was supplied with water at 10-11 o'clock every morning, and intake amount of diet and body weight was measured every day and once of three days, respectively. The body weight was measure at 2 hrs after removing feed bin to block sudden change of body weight according to feed intake, and feed efficiency was calculated by dividing body weight gain by amount of total intake amount of diet during total experimental period which is from initial day supplying experimental diet to sacrificed day. After experimental animals were fasted for above 12 hrs, they were anesthetized with diethylether, and their blood, liver and visceral fat tissues (epididymal fat, perirenal fat, mesenteric fat and abdominal fat) were collected. And then, they were washed with 0.1 M phosphate-buffered saline (pH 7.4), and their weights were measured. Blood taken from abdominal aorta was centrifuged at 1,000×g for 15 min to separate plasma.

Change of Body and Visceral Fat Weight

Body weight gain after diet was intaken during 8-week, was significantly reduced at a range of 25-60% in test group fed with 8 sesquiterpene compounds compared to HFD. Of them, body weight of test group fed with methyl cedryl ketone was most remarkably reduced, and body weight gain for 8-week was reduced to about 80% compared to control. On the other hand, body weight gain fed with other sesquiterpene compounds compared with control was reduced in the following order: (−)-α-cedrene, (+)-β-cedrene, cedryl acetate, methyl cedryl ether, cedrenol, (+)-cedrol and cedrene epoxide ($P<0.05$). Total visceral fat weight adding epididymal fat, perirenal fat, mesenteric fat and abdominal fat was measured after diet was fed during 8-week. As results, total visceral fat weight of all test groups fed with 8 sesquiterpene compounds was significantly reduced to 25-55% compared to control ($P<0.05$). Of them, visceral fat weight in test group fed with methyl cedryl ketone was most notably reduced, and next, the reduction effect of visceral fat weight in order of (−)-α-cedrene, (+)—O-cedrene, cedryl acetate, methyl cedryl ether, cedrenol and cedrene epoxide was measured ($P<0.05$). Visceral fat weight in test group fed with (+)-cedrol was higher than that in control. Therefore, it could be appreciated that all 8 sesquiterpene compounds in a level of 2% (wt/wt, additive diet amount) have excellent effect on reduction of body weight, and 7 sesquiterpene compounds except (+)-cedrol have remarkable effect on reduction of visceral fat weight (Table 6).

TABLE 6

Body weight gain and weight of total visceral fat weight in mice fed with the composition of the present invention.

| Group | Body weight gain (g/8 weeks) | total visceral fat weight (mg/g body weight) |
|---|---|---|
| Control | 16.6 ± 1.1 | 87.6 ± 5.50 |
| Cedryl acetate | 8.54 ± 0.84* | 46.4 ± 3.12* |
| Methyl cedryl ether | 9.31 ± 0.91* | 50.8 ± 6.12* |
| (−)-α-cedrene | 6.73 ± 1.02* | 40.0 ± 4.31* |
| (+)-β-cedrene | 7.13 ± 0.89* | 48.0 ± 8.27* |
| Cedrene epoxide | 12.4 ± 1.36* | 65.6 ± 4.43* |
| Methyl cedryl ketone | 6.51 ± 1.40* | 39.4 ± 7.44* |
| Cedrenol | 9.51 ± 1.47* | 57.8 ± 4.02* |
| (+)-cedrol | 10.9 ± 0.85* | 92.4 ± 5.31 |

*Significantly different from the value for HFD group by Student's t-test at $P < 0.05$.

Example 6

Efficacy on Prevention and Treatment of 8 Sesquiterpene Compounds for Hyperlipidemia Associated with Obesity, Fatty Liver and Type II Diabetes Concentration of total Plasma cholesterol, triglyceride and glucose was measured twice according to commercially available measurement kit (Bio Clinical system), respectively. Insulin concentration was measured by ELISA using mouse insulin kit (Shibayaki, Japan). Lipid component of liver tissue was extracted according to the method of Folch et al. 0.25 g of liver tissue was mixed with 1 ml distilled water, and homogenized with polytron homogenizer (IKA-WERKE GmbH & Co., Ultra-Turrax, Staufen, Germany). The homogenate was mixed with 5 ml of chloroform:methanol solution (2:1, v/v), and centrifuged at 1,000×g for 10 min to separate lower phase. Again, the supernant was mixed with 2 ml of chloroform:methanol solution (2:1, v/v), and the same procedure was repeated to isolate lipid component of liver tissue completely. Three ml of chloroform:methanol:0.05% $CaCl_2$ solution (3:48:47, v/v/v) were added to the resulting lower phase, and thoroughly mixed for 1 min. The mixture was centrifuged at 1,000×g for 10 min. The final lower phase was completely dried on nitrogen gas, and the dried lipid was dissolved in 1 ml of methanol to use analysis of lipid component. Triglyceride concentration in lipid extracts from liver tissues was measured according to commercially available measurement kit (Bio Clinical system) equal to that used in analysis of plasma.

In plasma lipid concentration of mouse fed with diet described in Table 5 for 8-week, total cholesterol concentration was significantly reduced to 46% in test group fed with methyl cedryl ether compared to HFD as shown in Table 7, and in addition to methyl cedryl ether, reduction of total cholesterol concentration in the order of (−)-α-cedrene, cedrenol, cedryl acetate, (+)-β-cedrene, methyl cedryl ketone, cedrene epoxide and (+)-cedrol compared with control was significantly measured at a range of 29-43%.

Plasma triglyceride concentration was significantly reduced to 50% in test group fed with (−)-α-cedrene compared to HFD and to 30% in test group fed with cedryl acetate and methyl cedryl ketone. Besides, plasma triglyceride concentration in test group fed with (+)-cedrol, (+)-β-cedrene and cedrene epoxide compared to HFD was significantly reduced at a range of 18-25%. Therefore, it could be appreciated that the above-described 8 sesquiterpene compounds remarkably alleviates hyperlipidemia shown in HFD-inducible obesity.

In addition, triglyceride concentration of liver tissue was significantly reduced to 64% and 63% in test group fed with (−)-α-cedrene and (+)-β-cedrene, respectively, and all test groups fed with methyl cedryl ketone, cedryl acetate, methyl cedryl ether, cedrenol and cedrene epoxide were significantly reduced at a range of 37-56% compared to HFD. Therefore, it could be demonstrated that 7 sesquiterpene compounds except (+)-cedrol has plausibly effect on amelioration of fatty-liver shown in HFD-inducible obesity.

It has been well-known that type II diabetes in which fasting glucose is simultaneously enhanced depending on increase in concentration of blood insulin was accompanied in dietary obesity animal model or human obesity. Recently, the term 'metaflammation' was emerged with respect to inflammation response generated by over-supply of nutrients or metabolites, obesity was considered as 'chronic and low-level inflammation', the researches on relationship between obesity and immune system has been intensively made. In other words, there has been newly emerged in the senses that various diabetes complications (e.g., type II diabetes, insulin resistance, arteriosclerosis, cancer and asthma) were generated through interactions with immune system during obesity development. For instance, it could be suggested that TLR4 (toll-like receptor 4) associated with innate immune response plays an important role in inflammation response and insulin resistance pathway using dietary fatty acid (particularly, saturated fatty acid) as a ligand, and is also related to regulation of food intake in the central nervous system.

According to the results in this experiment feeding cedryl acetate to mouse fed with HFD for 8-week, fasting glucose and blood insulin concentration in test group compared to HFD were significantly reduced to 54% and 49%, respectively. In addition, insulin resistance index (IR1) in test group was remarkably reduced to 73% compared to HFD. All fasting glucose (to 29-46% level), blood insulin concentration (to 26-40% level) and insulin resistance index (to 42-63% level) in test groups fed with methyl cedryl ether, (−)-α-cedrene, (+)-β-cedrene, methyl cedrene ketone, cedrenol and cedrene epoxide were remarkably reduced in comparison with those in control. In test group fed with (+)-cedrol, all fasting glucose, blood insulin concentration and insulin resistance index were prone to be decreased in comparison with control, but statistical significance was not shown. Therefore, it is expected that these sesquiterpene compounds have an effect on improvement of not only type II diabetes or insulin resistance, but also metabolic inflammation responses closely associated thereof.

TABLE 7

Biochemical index associated with obesity of mouse blood and liver tissue fed with the sesquiterpene compounds.

| | Plasma | | | | | Liver |
| Group | Total cholesterol (mmol/L) | Triglyceride (mmol/L) | Glucose (mmol/L) | Insulin (ng/mL) | IRI$^a$ | Triglyceride (μmol/g) |
| --- | --- | --- | --- | --- | --- | --- |
| Control | 3.71 ± 0.11 | 1:61 ± 0.01 | 10.3 ± 0.50 | 0.96 ± 0.10 | 1.63 ± 0.21 | 44.3 ± 2.33 |
| Cedryl acetate | 2.53 ± 0.10* | 1.12 ± 0.06* | 4.67 ± 0.40* | 0.49 ± 0.07* | 0.44 ± 0.06* | 23.8 ± 2.33* |
| Methyl cedryl ether | 2.01 ± 0.24* | 1.29 ± 0.13* | 5.61 ± 0.53* | 0.67 ± 0.07* | 0.61 ± 0.08* | 24.4 ± 1.37* |
| (−)-α-cedrene | 2.11 ± 0.16* | 0.81 ± 0.15* | 6.41 ± 0.57* | 0.67 ± 0.04* | 0.75 ± 0.13* | 16.1 ± 0.60* |
| (+)-β-cedrene | 2.57 ± 0.19* | 1.32 ± 0.11* | 6.80 ± 0.41* | 0.70 ± 0.08* | 0.78 ± 0.11* | 16.6 ± 1.28* |
| Cedrene epoxide | 2.81 ± 0.18* | 1.32 ± 0.08* | 7.34 ± 0.68* | 0.71 ± 0.04* | 0.94 ± 0.14* | 27.8 ± 2.41* |
| Methyl cedryl ketone | 2.60 ± 0.31* | 1.12 ± 0.11* | 6.88 ± 0.71* | 0.65 ± 0.06* | 0.78 ± 0.10* | 19.5 ± 1.30* |
| Cedrenol | 2.42 ± 0.22* | 1.20 ± 0.10* | 7.24 ± 0.56* | 0.58 ± 0.07* | 0.71 ± 0.09* | 25.0 ± 1.81* |
| (+)-cedrol | 2.98 ± 0.20* | 1.31 ± 0.10* | 9.8 ± 0.99 | 0.86 ± 0.07 | 1.45 ± 0.22 | 49.1 ± 4.10 |

*Significantly different from the value for HFD group by Student's t-test at P < 0.05.
$^a$IRI (insulin resistance index) = $10^{-3}$ pmol insulin × mmol glucose × $L^{-2}$ Having described a preferred embodiment of the present invention, it is to be understood that variants and modifications thereof falling within the spirit of the invention may become apparent to those skilled in this art, and the scope of this invention is to be determined by appended claims and their equivalents.

What is claimed is:

1. A method for treating hyperlipidemia, fatty liver, diabetes or obesity, comprising administrating to a subject in need thereof an effective amount of a sesquiterpene compound of formula (I);

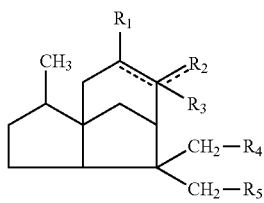

(I)

wherein:

$R_1$ is hydrogen, hydroxy, halogen, $C_1$-$C_3$ alkyl or —CO—$R_6$, wherein $R_6$ is hydrogen or $C_1$-$C_3$ alkyl;

$R_2$ is hydrogen, hydroxy or $C_1$-$C_3$ alkyl, or $R_1$ and $R_2$ may be taken together to form an epoxide;

$R_3$ is hydrogen, hydroxy, $C_1$-$C_3$ alkyl, —O—CO—$R_7$ or $C_1$-$C_3$ alkoxy, wherein $R_7$ represents hydrogen or $C_1$-$C_3$ alkyl;

$R_4$ is hydrogen, hydroxy or $C_1$-$C_3$ alkoxy;

$R_5$ is hydrogen, hydroxy or $C_1$-$C_3$ alkoxy; and

˭˭˭˭˭ represents a single or a double bond, wherein when ˭˭˭˭˭ in the ring is a double bond $R_2$ is hydrogen, hydroxy or $C_1$-$C_3$ alkyl, and when the bond ˭˭˭˭˭ between $R_2$ and the ring is a double bond, $R_2$ is $CH_2$;

with proviso that when $R_2$ is $C_1$ alkyl, $R_3$ is hydroxy, and that when $R_5$ is hydrogen, $R_4$ is not hydrogen.

2. The method of claim 1, wherein the sesquiterpene compound is administered as a pharmaceutical composition comprising the sesquiterpene compound and a pharmaceutically acceptable carrier, or a food composition comprising the sesquiterpene compound.

3. The method of claim 1, wherein the sesquiterpene compound is selected from the group consisting of cedryl acetate of formula (IV), α-cedrene of formula (V), μ-cedrene of formula (VI), cedrene epoxide of formula (IX), methyl cedryl ether of formula (XI), methyl cedryl ketone of formula (XIV), and cedrenol of formula (XV):

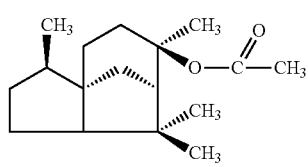

(IV)

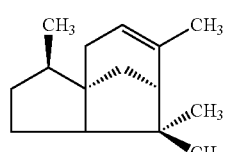

(V)

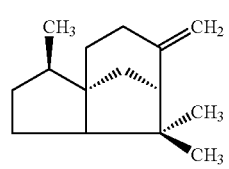
(VI)
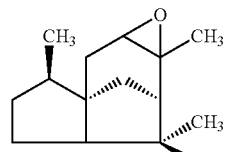
(IX)
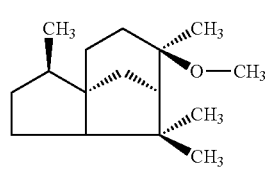
(XI)
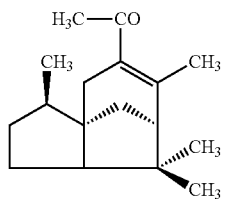
(XIV)
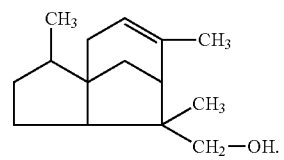
(XV)
* * * * *